United States Patent [19]

Mrozik

[11] Patent Number: 4,469,682

[45] Date of Patent: Sep. 4, 1984

[54] AVERMECTIN AND MILBEMYCIN PHOSPHATE ESTERS, PHARMACEUTICAL COMPOSITIONS, AND METHOD OF USE

[75] Inventor: Helmut H. Mrozik, Matawan, N.J.

[73] Assignee: Merck & Co., Inc., Rahway, N.J.

[21] Appl. No.: 461,843

[22] Filed: Jan. 28, 1983

[51] Int. Cl.³ .................. A61K 31/70; C07H 17/08; C07D 493/22

[52] U.S. Cl. .................. 424/180; 424/279; 536/7.1; 549/220; 549/264

[58] Field of Search .............. 424/180, 279; 549/220, 549/264, 260; 536/7.1

[56] References Cited

U.S. PATENT DOCUMENTS

| | | | |
|---|---|---|---|
| 2,490,573 | 12/1949 | Atherton et al. | 536/117 |
| 3,437,652 | 4/1969 | Campbell et al. | 536/117 |
| 3,950,360 | 4/1976 | Aoki et al. | 260/343.2 R |
| 4,134,973 | 1/1979 | Fisher et al. | 536/7.1 |
| 4,156,720 | 5/1979 | Fisher et al. | 536/7.1 |
| 4,161,583 | 7/1979 | Wilson et al. | 536/7.1 |
| 4,171,314 | 10/1979 | Chabala et al. | 260/343.41 |
| 4,173,571 | 11/1979 | Chabala et al. | 260/343.41 |
| 4,199,569 | 4/1980 | Chabala et al. | 424/180 |
| 4,201,861 | 5/1980 | Mrozik et al. | 424/180 |
| 4,206,205 | 6/1980 | Mrozik et al. | 424/180 |
| 4,310,519 | 1/1982 | Albers-Schonberg et al. | 424/181 |

Primary Examiner—Johnnie R. Brown
Attorney, Agent, or Firm—David L. Rose; Hesna J. Pfeiffer

[57] ABSTRACT

There are disclosed novel avermectin and milbemycin compounds wherein the various hydroxy groups are substituted with a phosphate ester group. The phosphate esters are prepared by reacting an avermectin or milbemycin compound with one or more unprotected hydroxy groups with a disubstituted halo phosphate. The avermectin and milbemycin phosphate esters have increased water solubility when compared with the parent compounds. The phosphate ester compounds have utility as anti-parasitic agents and compositions for that use are also disclosed. The compounds are also highly potent insecticides against agricultural pests.

19 Claims, No Drawings

AVERMECTIN AND MILBEMYCIN PHOSPHATE ESTERS, PHARMACEUTICAL COMPOSITIONS, AND METHOD OF USE

BACKGROUND OF THE INVENTION

The term avermectin (previously referrred to as C-076) is used to describe a series of compounds isolated from the fermentation broth of an avermectin producing strain of *Streptomyces avermitilis* and derivatives thereof. The morphological characteristics of the culture are completely described in U.S. Pat. No. 4,310,519. The avermectin compounds are a series of macrolides, each of which is substituted thereon at the 13-position with a 4'-(α-L-oleandrosyl)-α-L-oleandrose group. The avermectin compounds and the instant derivatives thereof have a very high degree of anthelmintic and anti-parasitic activity.

The avermectin series of compounds isolated from the fermentation broth having the following structure:

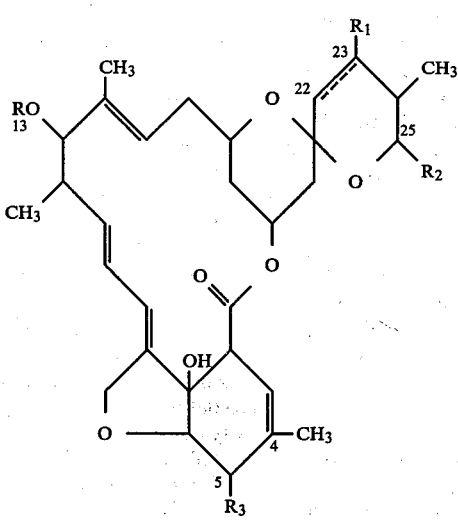

wherein R is the 4'-(α-1-oleandrosyl)-α1-oleandrose group of the structure:

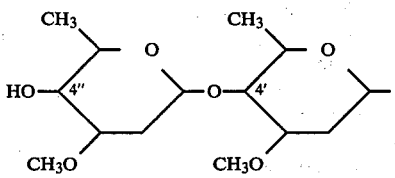

and wherein the broken line indicates a single or a double bond;

$R_1$ is hydroxy and is present only when said broken line indicates a single bond;
$R_2$ is iso-propyl or sec-butyl; and
$R_3$ is methoxy or hydroxy.

There are eight different major avermectin natural product compounds and they are given the designations A1*a*, A1*b*, A2*a*, A2*b*, B1*b*, and B2*a* based upon the structure of the individual compounds.

In the foregoing structural formula, the individual avermectin compounds are as set forth below. (The R group is 4'(α-L-oleandrosyl)-α-L-oleandrose):

|     | $R_1$       | $R_2$     | $R_3$   |
|-----|-------------|-----------|---------|
| A1a | Double Bond | sec-butyl | —OCH$_3$ |
| A1b | Double Bond | iso-propyl| —OCH$_3$ |
| A2a | —OH         | sec-butyl | —OCH$_3$ |
| A2B | —OH         | iso-propyl| —OCH$_3$ |
| B1a | Double Bond | sec-butyl | —OH     |
| B1b | Double Bond | iso-propyl| —OH     |
| B2a | —OH         | sec-butyl | —OH     |
| B2b | —OH         | iso-propyl| —OH     |

The avermectin compounds are generally isolated as mixtures of a and b components. Such compounds differ only in the nature of the $R_2$ substituent and the minor structural differences have been found to have very little effect on the isolation procedures, chemical reactivity and biological activity of such compounds.

Milbemycin compounds are similar to the above avermectin compounds in that the 16-membered macrocyclic ring is present. However, such compounds have no substitution at the 13-position and have a methyl or ethyl group at the 25-position (the position the $R_2$ group is found in the above structure). To the extent that such milbemycin compounds have hydroxy groups or can be converted to compounds with hydroxy groups which can then be substituted with the instant phosphate groups, they are to be construed as being within the ambit of this invention. Such milbemycin compounds and the fermentation conditions used to prepare them are described in U.S. Pat. No. 3,950,360. In addition, 13-deoxyavermectin aglycones are prepared synthetically from the avermectin natural products and are disclosed in U.S. Pat. Nos. 4,171,134 and 4,173,571. Such compounds are very similar to the milbemycins differing from some of the milbemycins in having an isopropyl or sec butyl rather than a methyl or ethyl group at the 25-position.

SUMMARY OF THE INVENTION

The instant invention is concerned with certain derivatives of avermectin and milbemycin compounds wherein the unprotected hydroxy groups are substituted with a phosphate ester. Thus it is an object of the instant invention to describe such avermectin and milbemycin phosphate ester compounds. A further object is to describe processes for the preparation of such compounds. A still further object is to describe the uses of such compounds as anti-parasitic agents. Still further objects will become apparent from a reading of the following description.

DESCRIPTION OF THE INVENTION

The compounds of the instant invention have the following structural formula

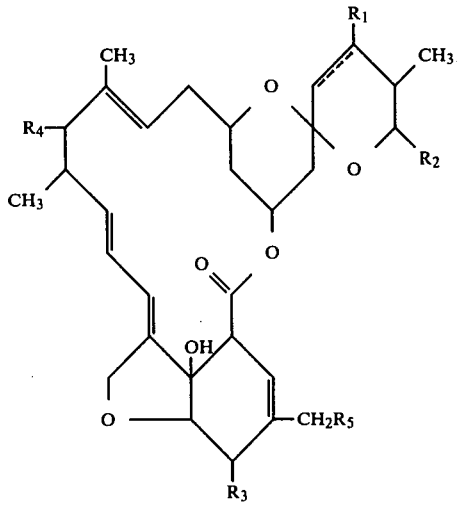

wherein the broken line indicates a single or double bond;

$R_1$ is H, =O, loweralkanoyloxy, OH, or OR provided that $R_1$ is present only when the broken line indicates a single bond;

$R_2$ is methyl, ethyl, isopropyl or sec-butyl;

$R_3$ is OH, $OCH_3$, loweralkanoyloxy or OR;

$R_4$ is H, OH, OR, loweralkanoyloxy, α-L-oleandrosyloxy, α-L-oleandrosyl-a-L-oleandrosyloxy, 4'-loweralkanoyl-α-L-oleandrosyloxy, 4''-loweralkanoyl-4'-α-L-oleandrosyl-α-L-oleandrosyloxy,

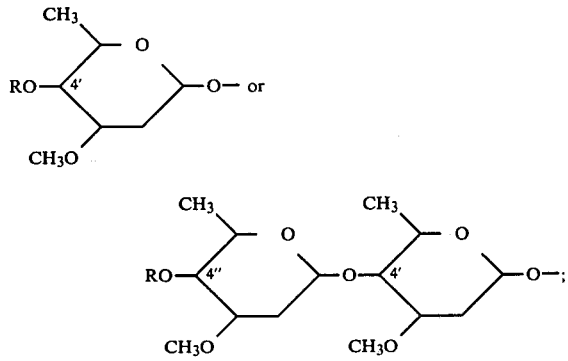

$R_5$ is H or OR; and

R is the phosphate ester groups P(O)(OH)(OMe), $P(O)(OMe)_2$, $P(O)(OCH_2CCl_3)_2$, $P(O)(OH)_2$, P(O)(OH)(OM), $P(O)(OM)_2$, $P(O)(OH)O^-(H_3N^+\text{-alk})$, $P(O)(O^-)_2(H_3N^+\text{alk})_2$, wherein M is an alkali metal, Me is a methyl group and alk is a loweralkyl; and physiologically acceptable salts thereof.

The term "loweralkyl" when used in the instant application is intended to represent those alkyl groups either straight or branched chain which have from 1–5 carbon atoms. Examples of such alkyl groups are methyl, ethyl, propyl, iso-propyl, butyl, sec-butyl, pentyl, and the like.

The term "loweralkanoyl" is intended to include those alkanoyl groups containing from one to five carbon atoms in either a straight or branched chain. Examples of such alkanoyl groups are formyl, acetyl, propionyl, butyryl, valeryl, and the like.

The term "halogen" is intended to include those halogen atoms fluorine, chlorine, bromine and iodine.

One aspect of the preferred compounds of this invention is realized in the above structural formula when R is $P(O)(OCH_2CCl_3)_2$. Further, examples of preferred compounds of the instant invention, and their physiologically acceptable salts, are:

4''-O-Acetyl-5-O-[di-(2,2,2-trichloroethyl)]phosphonoavermectin B1a/B1b;

4'',5-di-O-[bis-(2,2,2-trichloroethyl)]phosphono-23-keto-avermectin B2a/B2b;

4'',5-di-O-phosphono-23-keto-avermectin B2a/B2b;

22,23-dihydro-4'',5-di-O-[bis-(2,2,2-trichloroethyl)phosphono]-avermectin B1a/B1b;

22,23-dihydro-4''-O-[bis-(2,2,2-trichloroethyl)phosphono]avermectin B1a/B1b;

22,23-dihydro-4''-O-phosphono avermectin B1a/B1b;

22,23-dihydro-4''-O-phosphono avermectin B1a/B1b monosodium salt;

13-deoxy-5-phosphono-avermectin B1a/B1b aglycone;

13-deoxy-5-phosphono-22,23-dihydro avermectin B1a/B1b aglycone;

13-deoxy-4a-hydroxy-4a-O-phosphono avermectin B1a/B1b aglycone;

13-deoxy-4a-hydroxy-4a-O-phosphono-22,23-dihydroavermectin B1a/B1b aglycone;

4''-O-phosphono avermectin avermectin B1a/B1b;

4'',5-di-O-phosphono avermectin B1a/B1b;

22,23-dihydro-5-O-phosphono avermectin B1a/B1b;

5-O-phosphono avermectin B1a/B1b.

The "b" compounds, those with a 25-isopropyl group, are very difficult to separate from the corresponding "a" compound with a 25-sec-butyl group and as such the compounds are generally isolated as mixtures of the two compounds. Thus references in the instant application to "a" compounds such as B1a, A1a, and the like, are construed to define the pure compound as well as those which actually contain a certain proportion of the corresponding "b" compound. Alternatively, this representation of a mixture is sometimes done by referring to the B1 or B2 compounds or by separating the "a" compound from the "b" compound by a slash (/) such as B1a/B1b, B2a/B2b and the like.

The compounds of the instant invention are prepared by reacting those compounds of Formula III wherein R is hydrogen at the position where the phosphate group is desired, with an appropriately substituted phosphorohalide. Generally the bis (2,2,2-trichloroethyl) substituted phosphate is used and the othe phosphate esters described above are prepared therefrom. The reaction is carried out in a dry, inert solvent such as tetrahydrofuran, methylene chloride, N,N-dimethylformamide, toluene, and the like and is complete in from 1 to 24 hours at from 0° to 50° C. It is advisable to include in the reaction mixture at least one molecular equivalent of a base to react with the hydrogen halide which is liberated during the course of the reaction. Preferred bases are tertiary amines such as triethylamine, diisopropylethylamine, 4-dimethylaminopyridine and the like. It is preferred to carry out the reaction at about 10° to 20° C. for from 1 to 3 hours.

The phosphate monoesters are prepared by reducing a substituted phosphate with a reducing agent such as zinc dust activated by silver or copper compounds. The reaction is carried out preferably with zinc and the activating agent in pyridine solution with acetyl acetone or a similar reagent, as chelating agent at about 20° to 100° C. for from 10 minutes to 16 hours.

The alkali metal salts are prepared from the unsubstituted phosphates by treatment with one or two equivalents of an alkali metal hydroxide. The reaction is carried out in aqueous or methanolicaqueous medium at room temperature. The reaction is very rapid and is generally complete upon the addition of a stoichiometric amount of the base.

The methy esters are prepared directly using the substituted halo phosphonate or are prepared from the unsubstituted phosphate and diazomethane. The reaction is carried out in an inert solvent preferably ether or methylene chloride. The reaction is generally complete in from ½ to 16 hours and is carried out at about room temperature.

The quaternary ammonium salts of the phosphate are prepared by the addition thereto of one or two equivalents of ammonia or an amine in an inert, volatile solvent at room temperature or with cooling where the reaction is exothermic. The reaction is very fast and is complete following the addition. The product is isolated by evaporating the solvent in high vacuum to a solid residue.

PREPARATION OF STARTING MATERIALS

The ultimate starting materials for the compounds of this invention are the avermectin and milbemycin fermentation products defined above. Thus it is apparent that additional reactions are required to prepare many of the starting materials for the instant compounds. Specifically, reactions are carried out at the 4', 4", 4a, 5, 13, 22, and 23-positions. It is generally preferred to prepare whatever substituents are required at these positions before carrying out the reaction to introduce the phosphate on the substrate. Such a procedure generally avoids undesirable side reactions. This technique is not required, however, and if desired other sequences may be used. In addition, during the phosphorylation reaction described above, it is necessary to protect any hydroxy groups where reaction with the chlorophosphate is not desired. With the appropriate positions protected, the reactions may be carried out with the chlorophosphate without affecting the remainder of the molecule. Subsequent to any of the above described reactions the protecting group may be removed and the unprotected product isolated. The protecting group employed is ideally one which may be readily synthesized, will not be affected by the reaction with the chlorophosphate and may be readily removed without affecting any other functions of the molecule. It is noted that the instant protected compounds are novel and have considerable antiparasitic activity. They are included within the ambit of the instant invention. One preferred type of protecting group for the avermectin and milbemycin type of molecule is the tri-substituted silyl group, preferably the trialkyl silyl group. One especially preferred example, is the t-butyl dimethylsilyl group. The reaction preparing the protected compound is carried out by reacting the hydroxy compound with the appropriately substituted silylhalide, preferably the silylchloride in an aprotic polar solvent such as dimethylformamide. Imidazole is added as a catalyst. The reaction is complete in from 1 to 24 hours at from 0° to 25° C. For the 5-position hydroxy group the reaction is complete in from ½ to 3 hours at from 0° C. to room temperature. This reaction is selective to the 5 position under the conditions above described and very little, if any, silylation is observed at other hydroxy substituted positions. If it is desired to protect the 23-hydroxy group a 4", 5,23-tri(phenoxyacetyl) derivative can be prepared. Basic hydrolysis will leave the highy hindered 23-O-substituent but will hydrolize the 5- and 4"-O-phenoxy acetyl groups leaving them available for reaction. The 5-position may be selectively protected as described above with t-butyldimethylsilyl, and the 4" group may be reacted.

The silyl group may be removed after the other contemplated reactions may be carried out. The silyl group or groups are removed by stirring the silyl compound in methanol catalyzed by a catalytic amount of an acid, preferably a sulfonic acid such as p-toluene sulfonic acid. The reaction is complete in about 1 to 12 hours at from 0° to 50° C.

Another of the starting materials used in the foregoing reaction scheme are those in which the 22,23 double bond of the A1 and B1 compounds has been reduced to a single bond. As is readily apparent from an analysis of the structure of avermectin starting materials there are 5 unsaturations in the "1"-series of compounds. Thus in the "1" series of compounds it is necessary to reduce the 22,23 double bond while not affecting the remaining four unsaturations or any other functional group present on the molecule in order to selectively prepare the 22,23 dihydro avermectins. It is necessary to select a specific catalyst for the hydrogenation, one that will selectively hydrogenate the least hindered from among a series of unsaturations. The preferred catalyst for such a selective hydrogenation procedure is one having the formula:

[(Ph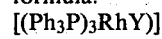3P)3RhY)]

wherein

Ph is phenyl and Y is halogen. The reduction procedure is completely described in U.S. Pat. No. 4,199,569 to Chabala et al.

Additional reactions which may be carried out to prepare the compounds of this invention are the selective removal of one or both of the α-L-oleandrosyl moieties (described in U.S. Pat. No. 4,206,205 to Mrozik et al.) or the selective acylation of the susceptible hydroxy groups (described in U.S. Pat. No. 4,201,861 to Mrozik et al.).

The reaction conditions which are generally applicable to the preparation of both the monosaccharide and aglycone involve dissolving the avermectin compound or the hydrogenated avermectin compound in an aqueous acidic non-nucleophilic organic solvent, miscible with water, preferably dioxane, tetrahydrofuran, dimethoxyethane, dimethylformamide, bis-2-methoxyethyl ether, and the like, in which the water concentration is from 0.1 to 20% by volume. Concentrated acid is added to the aqueous organic solvent to the extent of 0.01 to 10% by volume. The reaction mixture is generally stirred at about 20°-40° C., preferably at room temperature, for from 6 to 24 hours. The lower concentration of acid, from about 0.01 to 0.1% will predominately produce the monosaccharide under the above reaction conditions. Higher acid concentrations, from about 1 to 10% will predominantly produce the aglycone under the above reaction conditions. Intermediate acid concentrations will generally produce mixtures of monosaccharide and aglycone. The products are isolated, and mixtures are separated by techniques such as column, thin layer preparative and high pressure liquid chromatography, and other known techniques.

The acids which may be employed in the above process include mineral acids and organic acids such as sulfuric, hydrohalic, phosphoric, trifluoroacetic, trifluoro methane sulfonic and the like. The hydrohalic acids are preferably hydrochloric or hydrobromic. The preferred acid in the above process is sulfuric acid.

A further procedure for the preparation of the monosaccharide or aglycone of the avermectin compounds or of the hydrogenated avermectin compounds utilizes a different solvent system for the monosaccharide and the aglycone. The procedure for the preparation of the monosaccharide uses 1% acid by volume in isopropanol at from 20°–40° C., preferably room temperature, for from 6 to 24 hours. For the preparation of the aglycone, 1% acid, by volume, in methanol under the foregoing reaction conditions has been found to be appropriate.

When this procedure is employed on the starting materials containing the 22,23-double bond, there is a possibility of an acid catalyzed addition of the solvent to the double bond. If such occurs, chromatographic purification will remove the by-product in order to allow for further reactions.

The acids listed above are appropriate for this process, and again sulfuric acid is the preferred acid.

The acylated compounds are prepared using acylation techniques in which the reaction conditions will vary, depending upon the reactivity of the hydroxy group being acylated. Where there is more than one hydroxy group to be acylated, different reaction conditions are employed to minimize the formation of mixtures. The acylation reactions are described completely in U.S. Pat. No. 4,201,861 to Mrozik et al.

The acylation reagents employed are generally the halide, preferably the chloride, of the above loweralkanoyl groups. That is the loweralkanoyl halide reagent is generally employed.

In addition, the acylation reagent could be in the form of the anhydride or of the halo formate. In the case of reactions carried out with the halide reagents, it is often advantageous to include in the reaction mixture a basic compound capable of reacting with and neutralizing the hydrogen halide which is liberated during the course of the reaction. Tertiary amines are preferred such as triethylamine, pyridine, dimethylamino pyridine, diisopropyl ethylamine and the like. The basic compound is required in equimolar amounts relative to the numbered moles of hydrogen halide being liberated, however excess amounts, even using the basic compound as a solvent, are not detrimental.

In the case of the A1 compounds of avermectin, or of the hydrogenated avermectin A1 compounds there is only a single hydroxy group, 4" hydroxy, which may be acylated. The formation of the monosaccharide or the aglycone still leaves only a single hydroxy group which may be acylated, that is the 4' or 13 hydroxy group.

In the case of the 4", 4' and 13 hydroxy groups of avermectin A1 compounds, the acylating reagent is dissolved in a suitable solvent, pyridine is preferred, and the acylating reagent added. The reaction is maintained at from 0° C. to room temperature for from 4 to 24 hours. The product is isolated using known techniques.

The A2 compounds have two available hydroxy groups, the 4"(4' or 13) or the 23 positions. The different hydroxy groups may be selectively acylated by controlling the reaction conditions.

The 4"(4' or 13) monoacyl compound may be prepared by using the reaction conditions described above for the A1 compound. Since the 23 hydroxy is less reactive than the 4"(4' or 13) position, mild reaction conditions (0° C.) will afford predominantly the monoacyl compound. Heating the reaction mixture at from room temperature to 100° C. for from 1 to 24 hours will produce the 4"(4' or 13), 23-diacyl compound. If the 23 monoacyl compound is desired, the diacyl compound is treated with aqueous base, such as sodium hydroxide, at room temperature for from 1 to 24 hours. The 4"(4' or 13) acyl group will be hydrolyzed leaving the 23 monoacyl compound.

The B1 compounds have 2 available hydroxy groups: at the 4"(4' or 13) and the 5-positions. However, the two hydroxy groups have similar reactivities. When the reaction of the acylating agent in pyridine is carried out at about room temperature for from 4 to 24 hours, the diacyl compound is recovered. When the reaction is carried out at 0° C. a mixture of the 4"(4' or 13) and 5 monoacyl compounds are recovered. To recover individual compounds, the mixture is placed on a chromatographic column or a preparative layer chromatographic plate of alumina or silica gel and the individual compounds are readily isolated. In addition, techniques such as high pressure liquid chromatography may be employed to separate mixtures of acylated compounds.

The B2 compounds have three hydroxy groups available for substitution: the 4"(4' or 13), 5 and 23 positions. The relative reactivity of the various hydroxy groups is the same as in the other series of compounds. Thus, the triacyl compound may be prepared by carrying out the reaction at from room temperature to 100° C. The 4"(4' or 13), 5 diacyl compound may be prepared by carrying out the reaction at no more than room temperature. At 0° C. a mixture of 4"(4' or 13), and 5 monoacyl compounds is recovered which is separable as described above. By varying the reaction conditions and sequence, and by hydrolyzing the undesired acyl groups, all combinations of mono and diacyl compound may be recovered. For example, to prepare the 23-acyl compound, the triacyl compound is hydrolyzed with aqueous base as described above to remove the 4"(4' or 13) and 5 acyl groups. Acylation of the 23 monoacyl compound at 0° C. will result in a mixture of the diacyl compounds which is readily separable.

The compounds wherein $R_4$ is hydrogen are prepared from the avermectin starting materials as described hereinbelow. The reaction at the 13-position can generally be carried out either before or after the other above described reactions.

The series of reactions at the 13-position commences with the removal of the α-L-oleandrosyl-α-L-oleandrose side chain as described above. The avermectin aglycone compounds are then halogenated with a suitably reactive benzenesulfonyl chloride or bromide in the presence of a base to produce the "13-deoxy-13-halo-avermectin-aglycone" compounds. The halogen is then removed in a reaction with a trialkyltinhydride to produce the "13-deoxyavermectin aglycone compounds." The aglycone compounds are prepared using procedures described above.

The procedures for the preparation of the 13-deoxy compounds are described in detail in U.S. Pat. Nos. 4,171,134 and 4,173,571 to Chabala et al.

The 23-hydroxy group is oxidized to the 23-keto group to form the compounds wherein $R_1$ is =O, using oxidizing agents such as pyridinium dichromate; oxalyl-chloride-dimethylsulfoxide; acetic anhydride-dimethylsulfoxide; chromic acid-dimethylpyrazole; pyrazole;

chromic acid; trifluoromethylacetic anhydride-dimethylsulfoxide; chromic acid-acetic acid; and the like. Oxalylchloride-dimethylsulfoxide is the preferred oxidizing agent. Suitably protected compounds, as described below, are employed. The reaction is carried out at from dry-ice bath temperatures to room temperature, preferably from dry-ice bath temperatures to 0° C. and is complete in from 1-24 hours. The reaction may be carried out in any solvent in which the starting materials are reasonably soluble, and which will not react with the oxidizing agent. Such solvents as dimethylformamide, dimethylsulfoxide, methylene chloride, chloroform, carbon tetrachloride and the like are acceptable. For pyridinium dichromate reactions, dimethylformamide and dimethylsulfoxide are preferred. For chromic acid-dimethylpyrazole reactions, methylene chloride is preferred. The compounds are isolated from the reaction mixture using procedures known to those skilled in the art.

The 4a-hydroxy compounds are prepared by oxidizing the 4a-unsubstituted compounds. The oxidation of the 4-methyl group must be carried out selectively. Although the 4-methyl is an allylic methyl group and thus susceptible to oxidation, there is another allylic methyl group present on the molecule, at the 14 position. In addition, there are numerous allylic methine protons, such as those at the 2, 6, 8a, 12, 13, 16 and 24, positions which are capable of being oxidized by mild oxidation agents. Thus, it was surprising that a process could be developed that was selective for the desired oxidation product.

The preferred process involves treating the 4-methyl compound with t-butyl hydroperoxide in the presence of a catalytic amount of selenium dioxide. Under these conditions the selenium dioxide actually oxidizes the 4-methyl to a 4a-hydroxy methyl and is itself reduced in the process. The t-butyl hydroperoxide oxidizes the reduced selenium compounds back to selenium dioxide for further oxidation of the molecule. In this way only a small, catalytic amount of the selenium dioxide is required.

The reaction is carried out in an inert solvent; one not susceptible to oxidation. Methylene chloride is preferred, however, ethyl acetate, tetrahydrofuran and the like may also be employed. The reaction temperature may be from 0° to 50° C., however, reaction at room temperature is preferred. Under these conditions the reaction is generally complete in from 1-48 hours, however, under the preferred condition the reaction is generally complet in about 24 hours.

The novel compounds of this invention have significant parasiticidal activity as anthelmintics, ectoparasiticides, insecticides and acaricides, in human and animal health and in agriculture.

The disease or group of diseases described generally as helminthiasis is due to infection of an animal host with parasitic worms known as helminths. Helminthiasis is a prevalent and serious economic problem in domesticated animals such as swine, sheep, horses, cattle, goats, dogs, cats and poultry. Among the helminths, the group of worms described as nematodes causes widespread and often times serious infection in various species of animals. The most common genera of nematodes infecting the animals referred to above are Haemonchus, Trichostrongylus, Ostertagia, Nematodirus, Cooperia, Ascaris, Bunostomum, Oesophagostomum, Chabertia, Trichuris, Strongylus, Trichonema, Dictyocaulus, Capillaria, Heterakis, Toxocara, Ascaridia, Oxyuris, Ancylostoma, Uncinaria, Toxascaris and Parascaris. Certain of these, such as Nematodirus, Cooperia and Oesphagostomum attack primarily the intestinal tract while others, such as Haemonchus and Ostertagia, are more prevalent in the stomach while still others such as Dictyocaulus are found in the lungs. Still other parasites may be located in other tissues and organs of the body such as the heart and blood vessels, subcutaneous and lymphatic tissue and the like. The parasitic infections known as helminthiases lead to anemia, malnutrition, weakness, weight loss, severe damage to the walls of the intestinal tract and other tissues and organs and, if left untreated, may result in death of the infected host. The substituted avermectin compounds of this invention have unexpectedly high activity against these parasites, and in addition are also active against Dirofilaria in dogs, Namatospiroides, Syphacia, Aspiculuris in rodents, arthropod ectoparasites of animals and birds such as ticks, mites, lice, fleas, blowfly, in sheep Lucilia sp., biting insects and such migrating diperous larvae as Hypoderma sp. cattle, Gastrophilus in horses, and Cuterebra sp. in rodents.

The instant compounds are also useful against parasites which infect humans. The most common genera of parasties of the gastro-intestinal tract of man are Ancylostoma, Necator, Ascaris, Strongyloides, Trichinella, Capillaria, Trichuris, and Enterobius. Other medically important genera of parasites which are found in the blood or other tissues and organs outside the gastrointestinal tract are the filiarial worms such as Wuchereria, Brugia, Onchocerca and Loa, Dracunculus and extra intestinal stages of the intestinal worms Strongyloides and Trichinella. The compounds are also of value against arthropods parasitizing man, biting insects and other dipterous pests causing annoyance to man.

The compounds are also active against household pests such as the cockroach, Blatella sp., clothes moth, Tineola sp., carpet beetle, Attagenus sp., and the housefly *Musca domestica.*

The compounds are also useful against insect pests of stored grains such as Tribolium sp., Tenebrio sp. and of agricultural plants such as2spider mites, (Tetranychus sp.), aphids, (Acyrthiosiphon sp.); against migratory orthopterans such as locusts and immature stages of insects living on plant tissue. The compounds are useful as a nematocide for the control of soil nematodes and plant parasites such as Meloidogyne spp. which may be of importance in agriculture. The compounds are active against other plant pests such as the southern army worm and Mexican bean beetle larvae.

These compounds may be administered orally in a unit dosage form such as a capsule, bolus or tablet, or as a liquid drench where used as an anthelmintic in mammals. The drench is normally a solution, suspension or dispersion of the active ingredient usually in water together with a suspending agent such as bentonite and a wetting agent or like excipient. Generally, the drenches also contain an antifoaming agent. Drench formulations generally contains from about 0.001 to 0.5% by weight of the active compound. Preferred drench formulations may contain from 0.01 to 0.1% by weight. The capsules and boluses comprise the active ingredient admixed with a carrier vehicle such as starch, talc, magnesium stearate, or di-calcium phosphate.

Where it is desired to administer the avermectin derivatives in a dry, solid unit dosage form, capsules, boluses or tablets containing the desired amount of active compound usually are employed. These dosage forms are prepared by intimately and uniformly mixing the active ingredient with suitable finely divided diluents, fillers, disintegrating agents and/or binders such as starch, lactose, talc, magnesium stearate, vegetable gums and the like. Such unit dosage formulations may be varied widely with respect to their total weight and content of the antiparasitic agent depending upon factors such as the type of host animal to be treated, the severity and type of infection and the weight of the host.

When the active compound is to be administered via an animal feedstuff, it is intimately dispersed in the feed or used as a top dressing or in the form of pellets which may then be added to the finished feed or optionally fed separately. Alternatively, the antiparasitic compounds of our invention may be administered to animals parenterally, for example, by intraruminal, intramuscular, intratracheal, or subcutaneous injection in which event the active ingredient is dissolved or dispersed in a liquid carrier vehicle. For parenteral administration, the active material is suitably admixed with an acceptable vehicle, preferably of the vegetable oil variety such as peanut oil, cotton seed oil and the like. Other parenteral vehicles such as organic preparation using solketal, glycerol formal, and aqueous parenteral formulations are also used. The active avermectin compound or compounds are dissolved or suspended in the parenteral formulation for administration; such formulations generally contain from 0.005 to 5% by weight of the active compound.

Although the antiparasitic agents of this invention find their primary use in the treatment and/or prevention of helminthiasis, they are also useful in the prevention and treatment of diseases caused by other parasites, for example, arthropod parasites such as ticks, lice, fleas, mites and other biting insects in domesticated animals and poultry. They are also effective in treatment of parasitic diseases that occur in other animals including humans. The optimum amount to be employed for best results will, of course, depend upon the particular compound employed, the species of animal to be treated and the type and severity of parasitic infection or infestation. Generally good results are obtained with our novel compounds by the oral administration of from about 0.001 to 10 mg per kg of animal body weight, such total dose being given at one time or in divided doses over a relatively short period of time such as 1-5 days. With the preferred compounds of the invention, excellent control of such parasties is obtained in animals by administering from about 0.025 to 0.5 mg per kg of body weight in a single dose. Repeat treatments are given as required to combat re-infections and are dependent upon the species of parasite and the husbandry techniques being employed. The techniques for administering these materials to animals are known to those skilled in the veterinary field.

When the compounds described herein are administered as a component of the feed of the animals, or dissolved or suspended in the drinking water, compositions are provided in which the active compound or compounds are intimately dispersed in an inert carrier or diluent. By inert carrier is meant one that will not react with the antiparasitic agent and one that may be administered safely to animals. Preferably, a carrier for feed administration is one that is, or may be, an ingredient of the animal ration.

Suitable compositions include feed premixes or supplements in which the active ingredient is present in relatively large amounts and which are suitable for direct feeding to the animal or for addition to the feed either directly or after an intermediate dilution or blending step. Typical carriers or diluents suitable for such compositions include, for example, distillers' dried grains, corn meal, citrus meal, fermentation residues, ground oyster shells, wheat shorts, molasses solubles, corn cob meal, edible bean mill feed, soya grits, crushed limestone and the like. The active hydrogenated avermectin compounds are intimately dispersed throughout the carrier by methods such as grinding, stirring, milling or tumbling. Compositions containing from about 0.005 to 2.0% by weight of the active compound are particularly suitable as feed premixes. Feed supplements, which are fed directly to the animal, contain from about 0.0002 to 0.3% by weight of the active compounds.

Such supplements are added to the animal feed in an amount to give the finished feed the concentration of active compound desired for the treatment and control of parastic diseases. Although the desired concentration of active compound will vary depending upon the factors previously mentioned as well as upon the particular avermectin derivative employed, the compounds of this invention are usually fed at concentrations of between 0.00001 to 0.002% in the feed in order to achieve the desired antiparasitic result.

The avermectin compounds of this invention are also useful in combatting agricultural pests that inflict damage upon crops while they are growing or while in storage. The compounds are applied using known techniques as sprays, dusts, emulsions and the like, to the growing or stored crops to effect protection from such agricultural pests.

In using the compounds of this invention, the individual substituted avermectin components may be prepared and used in that form. Alternatively, mixtures of two or more of the individual avermectin components may be used, as well as mixtures of the parent avermectin compounds, other avermectin compounds or other active compounds not related to avermectin, with the compounds of this invention.

In the isolation of the avermectin compounds, which serve as starting materials for the instant proceses, from the fermentation broth, the various avermectin compounds will be found to have been prepared in unequal amounts. In particular an "a" series compound will be prepared in a higher proportion than the corresponding "b" series compound. The difference between the "a" series and "b" series is constant throughout the avermectin compounds and consists of a sec-butyl group and an iso-propyl group respectively at the 25 position. This difference, of course, does not interfere with any of the instant reactions. In particular it may not be necessary to separate the "b" components from the related "a" component. Separation of these closely related compounds is generally not practiced since the "b" compound is present only in a very small percent by weight, and the structural difference has negligible effect on the reaction processes and biological activities.

In particular it has been found that the starting materials for the compounds of this invention are very often prepared in a ratio of about 80% avermectin B1a or A1a and 20% avermectin B1b or A1b. Thus the preferred composition of this invention is one which contains about 80% of the "a" component and 20% of the "b" component.

The following examples are provided in order that this invention might be more fully understood; they are not to be construed as limitative of the invention.

The substituted avermectin derivatives prepared in the following examples are generally isolated as amorphous solids and not as crystalline solids. They are thus characterized analytically using techniques such as mass spectrometry, nuclear magnetic resonance, and the like. Being amorphous, the compounds are not characterized by sharp melting points, however, the chromatographic and analytical methods employed indicate that the compounds are pure.

In the following examples, the various starting materials therefor are avermectin compounds or derivatives of avermectin compounds. The avermectin compounds and the preparation and isolation thereof from fermentation broths are described in U.S. Pat. No. 4,310,519 issued 12 Jan. 1982. The selective 22, 23-dihydro derivatives of avermectin compounds are described in U.S. Pat. No. 4,199,569 issued 22 Apr. 1980. The aglycone and monosaccharide derivatives of avermectin compounds are described in U.S. Pat. No. 4,206,205 issued 3 Jan. 1980.

EXAMPLE 1

4''-O-Acetyl-5-O-[bis-(2,2,2-trichloroethyl)phosphono] avermectin B1a/B1b

50 Mg (0.055 mmol) of 4''-O-acetyl avermectin B1a/B1b was dissolved in 1.0 ml of dry tetrahydrofuran and stirred at room temperature while 0.1 ml (0.55 mmol) of diisopropylethylamine was added followed in one portion by 95 mg (0.25 mmol) of bis(2,2,2-trichloroethyl)phosphorochloridate and 10 mg (0.08 mmol) of 4-dimethylaminopyridine. The reaction was stirred for 3½ hours whereupon analysis by thin layer chromatography indicated that the reaction was essentially complete. 7 Ml of ether was added and the reaction mixture washed with water, dilute aqueous hydrochloric acid, aqueous sodium bicarbonate, and water. The organic layer was dried and concentrated in vacuo to 69 mg of a colorless glass which was identified by nuclear magnetic resonance as 4''-O-acetyl-5-O-[(bis-2,2,2-trichloroethyl)phosphono] avermectin B1a/B1b.

EXAMPLE 2

4'',5-Di-O-[bis-(2,2,2-trichloroethyl)phosphono]-23-keto avermectin B2a/B2b

100 Mg of 23-keto avermectin B2a/B2b was dissolved in 1 ml of dry tetrahydrofuran with stirring at room temperature. Then 0.18 ml of diisopropylethylamine was added followed by 190 mg of bis-(2,2,2-trichloroethyl)phosphorochloridate. The reaction became homogeneous and in a short time formed a precipitate. 20 Mg of 4-dimethylaminopyridine was added to the heterogenous reaction mixture and stirred at room temperature for 30 minutes. Thin layer chromatographic analysis indicated that the reaction was not yet completed, thus an additional 1 ml of dry tetrahydrofuran, 0.18 ml of diisopropylethylamine, 190 mg of bis-(2,2,2-trichloroethyl)phosphorochloridate and 20 mg of 4-dimethylaminopyridine was added and the reaction mixture stirred for 25 minutes. At this time, thin layer chromatographic analysis indicated that the reaction had proceeded to completion. The tetrahydrofuran was removed in a stream of dry nitrogen and the residue diluted with water and ether. The mixture was extracted 3 times with ether and the combined organic layers washed 3 times with 1N hydrochloric acid, twice with water and once with dilute disodium bicarbonate solution, once again with water and once with saturated sodium chloride. The organic layer was dried over magnesium sulfate and evaporated to dryness in vacuo affording 223.7 mg of a colorless glass. This glass was purified by preparative layer chromatography on silica gel plates of 2000 micron thickness with 20% ethyl acetate in methylene chloride as the mobile phase affording 161 mg of a colorless glass which 300 MHz nuclear magnetic resonance and mass spectrometry indicates to be the desired product.

EXAMPLE 3

4'',5-Di-O-phosphono-23-keto avermectin B2a/B2b

Part A: Preparation of zinc/silver reagent

In a 25 ml 1-neck round-bottom flask 10 ml of 2.5N hydrochloric acid was stirred vigorously at room temperature and 2.1 grams of zinc dust was added all at once. The mixture is stirred for 4 minutes and the liquid removed by decantation. The residue was washed twice with 10 ml of acetone, once with 10 ml of ether and the residue added to a hot suspension of 70 mg of silver acetate and 10 ml of glacial acetic acid. The mixture was stirred for one minute and the liquid was decanted from the still warm reaction mixture. The residue was washed once with 5 ml of glacial acetic acid, 4 times with 10 ml of ether and stored under 10 ml of methanol.

Part B: Reduction Reaction

40 Mg of 4'',5-di-[bis-O-(2,2,2-trichloroethyl)phosphono]-23-keto avermectin B2a/B2b was dissolved in 1 ml of a 9:1 pyridine/water mixture in a 10 ml 3-neck round-bottom flask with vigorous stirring. Freshly prepared zinc/silver reagent, 30 to 40 mg, was added. The reaction was immersed in an oil bath preheated to 125° C. The reaction was brought to reflux over 1½ minutes and refluxed for 5 minutes. An additional 30 to 40 mg of moist zinc/silver reagent was added and refluxed for an additional 5 minutes. A final portion of 30 to 40 mg of zinc/silver reagent was added and the reaction mixture refluxed for 5 minutes. The reaction was cooled and transferred to a centrifuge tube. The insolubles were centrifuged and the liquid removed by decantation. The residue was washed twice with 1 ml of 9:1 pyridine/water mixture and the liquid layers were combined and evaporated to a volume of about 0.2 ml under a stream of nitrogen. The residue was diluted with 5 ml of ethyl acetate and acidified with 1N hydrochloric acid. The phases were separated and the aqueous layer washed twice with ethyl acetate. The organic layers were combined, washed 5 times with dilute sodium chloride solution, once with saturated sodium chloride and dried over magnesium sulfate. The organic layer was evaporated under a stream of nitrogen and pumped dry under high vacuum affording 22.5 mg of 4'',5-di-O-phosphono-23-keto avermectin B2a/B2b as a light glass. The purity was checked by high pressure liquid chromatography on a Waters $C_{18}$ micro-bondapak column and methanol:water-65:35 as the mobile phase.

EXAMPLE 4

22,23-dihydro-4'',5-di-O-[bis-(2,2,2-trichloroethyl)phosphono]avermectin B1a/B1b 100 Mg of 22,23-dihydro avermectin B1a/B1b in 1 ml of dry tetrahydrofuran was added to 0.18 ml of N,N- diisopropylethylamine and stirred. To the mixture was added 190 mg of bis-(2,2,2-trichloroethyl)phosphorochloridate. The reaction was stirred for 2 minutes and 20 mg of 4-dimethylaminopyridine was added and the reaction mixture stirred for 90 minutes. Thin layer chromatography indicated that the reaction was not complete. Thus, 1 ml of dry tetrahydrofuran containing 0.18 ml of diisopropylethylamine, 190 mg of bis(2,2,2-trichloroethyl)phosphorochloridate and 20 mg of 4-dimethylaminopyridine was added and the reaction mixture stirred for an additional 25 minutes. The solvent was removed under a stream of nitrogen, ether and water were added and the layers separated. The water layer was extracted twice with ether and the organic layers combined and washed three times with dilute hydrochloric acid, once with dilute sodium bicarbonate and once with water. The organic layer was dried over magnesium sulfate and evaporated to dryness under a stream of nitrogen affording 200 mg of a beige foam. All of the foam was dissolved in methylene chloride and placed on 2 preparative layer chromatography plates containing a 1,000 micron thick layer of silica gel and eluted with a mixture of 5% tetrahydrofuran and 0.15% ethanol in methylene chloride affording 120 to 140 mg of clear glass which 300 MHz nuclear magnetic resonance indicated to be 22,23-dihydro-4″,5-di-O-[bis-(2,2,2-trichloroethyl)phosphono]avermectin B1a/B1b.

EXAMPLE 5

22,23-dihydro-4",5-di-O-phosphono avermectin B1a/B1b

The zinc/silver reagent was prepared as described in Example 3 using 2.1 gm of zinc dust, 10 ml of 2.5N hydrochloric acid and 60 to 70 mg of silver acetate in 10 ml of acetic acid. To a mixture of 40 mg of 22,23-dihydro-4",5-di-O-[bis-(2,2,2-trichloroethyl)phosphono] avermectin B1a/B1b in 1 ml of a 9:1 mixture of pyridine and water was added 30 to 40 mg of the freshly prepared zinc/silver reagent and the reaction mixture heated in an oil bath at 125° C. The mixture was refluxed for 5 minutes and another 30 to 40 mg portion of the zinc/silver reagent was added and refluxed for 5 minutes. A final portion of 30 to 40 mg of the zinc/silver reagent was added and the refluxing continued for 5 minutes. The reaction mixture was cooled and centrifuged and the residue washed twice with a 9:1 mixture of pyridine in water. The solutions were combined and evaporated to a small volume. Ethyl acetate was added and made acidic with dilute hydrochloric acid solution. The aqueous layer was extracted again with ethyl acetate and the organic layers combined and washed 5 times with dilute sodium chloride solution and once with saturated sodium chloride solution. The organic layer was dried over magnesium sulfate and evaporated under a stream of nitrogen affording 23 mg of a brown glass which 300 MHz nuclear magnetic resonance indicated to be 22,23-dihydro-4",5-di-O-phosphono avermectin B1a/B1b.

EXAMPLE 6

22,23-Dihydro-5-O-t-butyldimethylsilyl-4"-O-[bis-(2,2,2-trichloroethyl)phosphono] avermectin B1a/B1b 5 Grams of 22,23-dihydro-5-O-t-butyldimethylsilyl avermectin B1a/B1b in 30 ml of tetrahydrofuran was stirred at room temperature and combined with 4.5 ml of N,N-diisopropylethylamine and 4.8 g of bis-(2,2,2-trichloroethyl)phosphorochloridate followed by 500 mg of 4-dimethylaminopyridine. The reaction mixture was stirred for 2½ hours whereupon another 1 ml of diisopropylethylamine 400 mg of bis-(2,2,2-trichloroethyl)-phosphorochloridate and 50 mg of dimethylaminopyridine was added and the reaction mixture stirred for a total of 4 hours. The reaction mixture was combined with 150 ml of cold water, extracted 4 times with 60 ml of ether and the combined ether layers washed 4 times with 50 ml of water and once with saturated sodium chloride solution. The organic layer was dried over magnesium sulfate and evaporated to dryness in vacuo affording 9.69 g of a light yellow foam. The foam was placed on a column with 300 g of Silica Gel 60 and eluted with 10% ethyl acetate in methylene chloride. The first liter of eluant was discarded and the second and third liters combined and concentrated to dryness in vacuo affording 6.70 g of a white foam identified as 22,23-dihydro-5-O-t-butyldimethylsilyl-4"-O-[bis-(2,2,2-trichloroethyl)phosphono] avermectin B1a/B1b.

EXAMPLE 7

22,23-dihydro-4"-O-[bis-(2,2,2-trichloroethyl) phosphono] avermectin B1a/B1b 6.7 Grams of 22,23-dihydro-5-O-t-butyldimethylsilyl-4"-O-[bis-(2,2,2-trichloroethyl) phosphono] avermectin B1a/B1b was dissolved in 300 ml of 1% p-toluene sulfonic acid monohydrate in methanol. The reaction mixture was stoppered and let stand at room temperature for 25 minutes. The reaction mixture was poured onto 300 ml of ice-cold dilute sodium bicarbonate solution, diluted with ether and the layers separated. The aqueous layer was extracted 3 more times with 80 ml portions of ether, combined and washed 3 times with 50 ml of water, once with sodium chloride solution and dried over magnesium sulfate. The organic layer was evaporated to dryness in vacuo affording 6.5 g of a white foam which was identified by its nuclear magnetic resonance spectrum as 22,23-dihydro-4"-O-[bis-(2,2,2-trichloroethyl)phosphono]avermectin B1a/B1b.

EXAMPLE 8

22,23-Dihydro-4"-O-phosphono avermectin B1a/B1b 2.5 Grams of 22,23-dihydro-4"-O-[bis-(2,2,2-trichloroethyl)phosphono] avermectin B1a/B1b was dissolved in 250 ml of glacial acetic acid and stirred vigorously under an atmosphere of nitrogen at room temperature. 10.0 Grams of zinc-silver complex (prepared as described in Example 3) was added and the reaction mixture was stirred vigorously for 3 hours at room temperature. The reaction mixture was filtered and the residue was washed with acetic acid. The filtrate was concentrated in high vacuum with a rotary evaporator in a water bath at about 35° C. leaving 3.58 g of a beige solid residue. The residue was treated with dilute aqueous hydrochloric acid and ethyl acetate. The layers were separated and the organic phase was washed with water repeatedly, dried over magnesium sulfate and concentrated in vacuo and under high vacuum to 2.24 g of a white foam which was identified as 22,23-dihydro-4"-O-phosphono avermectin B1a/B1b.

EXAMPLE 9

22,23-Dihydro-4"-O-phosphono avermectin B1a/B1b Monosodium Salt 1.3 Grams of 22,23-dihydro-4"-O-phosphono avermectin B1a/B1b was combined with 25 ml of 0.025 molar sodium hydroxide solution with stirring. An additional 35 ml of 0.025 molar sodium hydroxide solution was added portionwise followed by 15 drops of methanol to give a clear solution with a final pH of 6.8. The solution was extracted with 75 ml of ethyl acetate and the layers separated. The aqueous layer was placed in a 2 liter round-bottom flask and freeze dried affording 1.08 g of a white lyophilized powder identified by high pressure liquid chromatography, nuclear magnetic resonance and elemental analysis as 22,23-dihydroavermectin B1a/B1b-4"-O-phosphate monosodium salt.

EXAMPLE 10

22,23-Dihydro-5-O-tert-butyldimethylsilyl-4"-O-(2,2,2-trichloroethylphosphono) avermectin B1a/B1b 8.4 G of 22,23-dihydro-5-O-t-butyl-dimethylsilyl avermectin B1a/B1b, 50 ml of freshly distilled tetrahydrofuran, and 7.6 ml of N,N-diisopropylethylamine were combined and stirred at room temperature. 9.7 G of bis(2,2,2-trichloroethyl)phosphorochloridate was added along with 750 mg of 4-dimethylaminopyridine. The reaction mixture was stirred at room temperature for 3½ hours and poured onto 250 ml of ice water. The aqueous solution was diluted with 100 ml of ether, separated and the aqueous phase extracted with 50 ml of ether. The ether extracts were combined and washed repeatedly with water, dried and concentrated in vacuo, under high vacuum to afford 17.4 gms of a light orange foam. The foam was purified on 500 g of silica gel in a column eluted with 10% ethyl acetate in methylene chloride which afforded 6.3 g of a light colored solid identified by nuclear magnetic resonance as 22,23-dihydro-5-O-t-butyldimethylsilyl4"-[bis-O-(2,2,2-trichloroethyl)phosphono]avermectin B1a/B1b. Elution of the column with 10% methanol in methylene chloride gave 3.98 g of a second product identified by nuclear magnetic resonance and mass spectrometry as 22,23-dihydro-5-O-tert-butyldimethylsilyl-4"-O-(2,2,2-trichloroethylphosphono) avermectin B1a/B1b.

EXAMPLE 11

22,23-Dihydro-5-O-[bis(2,2,2-trichloroethyl)phosphono] avermectin B1a/B1b

Following the procedure of Example 1 using 10.0 g of 22,23-dihydro avermectin B1a/B1b, 150 ml of tetrahydrofuran, 4.5 ml of N,N-diisopropylethylamine, 4.4 g of bis(2,2,2-trichlorethyl)phosphorochloridate and 600 mg of 4-dimethylaminopyridine there was obtained 10.1 g of 5-O-[bis-(2,2,2-trichloroethyl)phosphono] 22,23-dihydro avermectin B1a/B1b.

EXAMPLE 12

5-O-t-butyldimethylsilyl 4"-O-[bis(2,2,2-trichloroethyl)phosphono] avermectin B1a/B1b Following the procedure of Example 1 using 9.3 g of 5.0 t-butyl dimethylsilyl avermectin B1a/B1b 55 ml of tetrohydrofuran, 8.3 ml of N,N-diisopropylethylamine, 10.7 g of bis(2,2,2-trichlorethyl)phosphorochloridate and 1 g of 4-dimethylaminopyridine, there was obtained after stirring for 30 minutes at room temperature, and silica gel column purification, 12.14 g of 5-O-t-butyl dimethylsilyl 4"-O-[-bis(2,2,2-trichloroethyl)-phosphono]avermectin B1a/B1b.

EXAMPLE 13

4"-O-[bis(2,2,2-trichloroethyl)phosphono]avermectin B1a/B1b

Following the procedure of Example 7 using 12.1 g of 5-O-t-butyl dimethylsilyl 4"-O-[bis(2,2,2-trichloroethyl)phosphono] avermectin B1a/B1b, 300 ml of 1% p-toluenesulfonic acid in methanol, there was obtained 9.88 g of 4"-O-[bis(2,2,2-trichloroethyl)phosphono] avermectin B1a/B1b.

EXAMPLE 14

4"-O-phosphono avermectin B1a/B1b

3 Grams of 4"-O-[bis-(2,2,2-trichloroethyl)phosphono] avermectin B1a/B1b dissolved in 65 ml of pyridine was treated with 7.0 ml of 2,4-pentanedione and 3 g of zinc-silver complex (prepared as described in Example 3) added in small portions with vigorous stirring at room temperature for 3 hours under an atmosphere of nitrogen. The reaction mixture was filtered and the filtrate concentrated under high vacuum to 8 g of a light brown foam. This was treated with 100 ml of 2.5 N aqueous hydrochloric acid and 100 ml of ethyl acetate. The layers were separated and the ethyl acetate extract washed repeatedly with water. The organic layer was dried and evaporated in vacuo and high vacuum to 2.4 g of a residue obtained as a light foam characterized by nuclear magnetic resonance, ultraviolet spectroscopy, thin layer chromatography, high pressure liquid chromatography, and elemental analysis as 4"-O-phosphono avermectin B1a/B1b.

EXAMPLE 15

4"-O-Phosphono Avermectin B1a/B1b monosodium salt 510 mg of 4"-O-phosphono avermectin B1a/B1b was combined with 15 ml of 0.025 M aqueous sodium hydroxide solution and stirred at room temperature until a solution was achieved or nearly achieved. Upon the addition of 1 ml of methanol all suspended material was dissolved and additional 0.025 M sodium hydroxide is added dropwise until the pH is brought to 6.9. Freeze drying the solution affords 490 milligrams of a white solid which was identified as 4"-O-phosphono avermectin B1a/B1b monosodium salt.

EXAMPLE 16

22,23-dihydro-4"-O-phosphono Avermectin B1a/B1b disodium salt 50 mg. of 22,23-dihydro-4"-O-phosphono avermectin B1a/B1b monosodium salt (obtained by following a procedure similar to that of Example 15) was combined with 0.5 ml of water and 2 ml of a 0.025 M sodium hydroxide solution and stirred until the suspension became quite thick, whereupon the addition of 0.5 ml of water reduced the viscosity. The pH of the final solution was 10.2. The reaction mixture was lyophilized to give 22,23-dihydro-4"-O-phosphono avermectin B1a/B1b disodium salt as a white fluffy powder.

EXAMPLE 17

22,23-Dihydro-4"-O-phosphono avermectin B1a/B1b dimethyl ester

10 Ml of 22,23-dihydro-4"-O-phosphono avermectin B1a/B1b was dissolved in 0.4 ml of methylene chloride and 0.6 ml of a diazomethane solution containing an excess of diazomethane was added. After standing for 30 minutes at room temperature, the reaction mixture was evaporated to dryness under a stream of nitrogen and the residue was dissolved in ethyl acetate, washed with water and dried over magnesium sulfate. Evaporation to dryness under a stream of nitrogen afforded 10 mg of a glass which is purified on preparative layer chromatography on silica gel layers 250 microns thick, eluting with 5% methanol in methylene chloride which afforded 8 mg of 22,23-dihydro-4"-O-phosphono avermectin B1a/B1b dimethyl ester.

EXAMPLE 18

5-O-Tert-butyldimethylsilyl-22,23-dihydro-4"-O-[methyl(2,2,2-trichloroethyl)phosphono] avermectin B1a/B1b Following the procedure of Example 17 using 15 mg of 22,23-dihydro-4"-O-(2,2,2-trichloroethyl phosphono) avermectin B1a/B1b, 0.6 ml of methylene chloride and 0.9 ml of diazomethane solution containing an excess of diazomethane, there was obtained 11 mg of 22,23-dihydro-4"-O-[methyl-(2,2,2-trichloroethyl)phosphono] avermectin B1a/B1b.

EXAMPLE 19

22,23-Dihydro-5-O-phosphono avermectin B1a/B1b

Following the procedure of Example 14 using 100 mg of 22,23-dihydro 5-O-[bis-(2,2,2-trichloroethyl)phosphono] avermectin B1a/B1b and 3 ml of pyridine, 0.2 ml of 2,4-pentanedione and 400 mg of a zinc silver mixture, there was obtained 90 mg of 22,23-dihydro-5-O-phosphono avermectin B1a/B1b.

EXAMPLE 20

Cyclohexylammonium 22,23-dihydroavermectin B1a/B1b 4"-O-phosphate

A solution of 100 mg of 22,23-dihydro-4"-O-phosphono avermectin B1a/B1b and 10.5 mg (1 equivalent, 12 μl) of cyclohexylamine in 3 ml of ethyl acetate was concentrated in vacuo and high vacuum to give 100 mg of a glass identified as cyclohexylammonium-22,23-dihydroavermectin B1a/B1b 4"-O-phosphate.

EXAMPLE 21

Bis-cyclohexylammonium-22,23-dihydro avermectin B1a/B1b 4"-O-phosphate

A solution of 50 mg of 22,23-dihydro-4"-O-phosphono avermectin B1a/B1b and 10.5 mg (2 equivalents, 12 μl) of cyclohexylamine in 1.5 ml of ethyl acetate was concentrated in vacuo and high vacuum to a colorless glass which was shown by elemental analysis to be bis-cyclohexylammonium-22,23-dihydro avermectin B1a/B1b 4"-O-phosphate.

EXAMPLE 22

[Bis-(2-hydroxyethyl)]ammonium avermectin B1a/B1b 4"-O-phosphate

Following the procedure of Example 21 using 100 mg of 4"-O-phosphono avermectin B1a/B1b 11 mg (1 equivalent, 10 μl) of diethanolamine and 3 ml of ethyl acetate there is obtained [bis-(2-hydroxyethyl)]ammonium avermectin B1a/B1b 4"-O-phosphate as a colorless glass.

EXAMPLE 23

Pyridinium 22,23-dihydro avermectin B1a/B1b 5-O-phosphate

A solution of 30 mg of 5-O-phosphono-22,23-dihydro avermectin B1a/B1b and 0.5 ml of pyridine is concentrated in vacuo and high vacuum to a colorless residue identified as pyridinium 22,23-dihydro avermectin B1a/B1b 5-O-phosphate.

EXAMPLE 24

Tert-butylammonium-13-deoxy-22,23-dihydro avermectin B1a/B1b aglycone-5-O-phosphate A solution of 50 mg of 13-deoxy-5-O-phosphono 22,23-dihydro avermectin B1a/B1b aglycone in 1 ml of tert-butylamine is evaporated in vacuo and high vacuum to afford a colorless glass identified as tert-butylammonium-13-deoxy-22,23-dihydro avermectin B1a/B1b aglycone-5-O-phosphate.

EXAMPLE 25

22,23-Dihydro-4"-O-[methyl(2,2,2-trichloroethyl)phosphono]avermectin B1a/B1b

Following the procedure of Example 7, using 650 mg of 5-O-tert-butyldimethylsilyl-22,23-dihydro4"-O-[methyl(2,2,2-trichloroethyl)phosphono]avermectin B1a/B1b in 65 ml of 1% p-toluenesulfonic acid monohydrate in methanol and further purification by preparative layer silica gel chromatography 400 mg of 22,23-dihydro-4"-O-[methyl(2,2,2-trichloroethyl)phosphono]avermectin B1a/B1b was obtained.

EXAMPLE 26

22,23-Dihydro-4"-O-(methyl-phosphono)avermectin B1a/B1b

Following the procedure of Example 14 using 50 mg of 22,23-dihydro-4"-O-[methyl(2,2,2-trichloroethyl)phosphono]avermectin B1a/B1b 2 ml of pyridine, 0.1 ml of 2,4-pentanedione and 100 mg of zinc, 40 mg of 22,23-dihydro-4"-O-(methyl-phosphono)avermectin B1a/B1b was obtained as a yellow glass.

EXAMPLE 27

13-Deoxy-22,23-dihydro-5-O-[bis-(2,2,2-trichloroethyl)phosphono]avermectin B1a/B1b aglycone Following the procedure of Example 1 using 1.0 g (1.75 mmol) of 13-deoxy-22,23-dihydro avermectin B1a/B1b aglycone, 10 ml of tetrahydrofuran, 1.17 g (1.575 ml) of di-isopropylethylamine, 1.68 g (4.4 mmol) of bis-(2,2,2-trichloroethyl)phosphorochloridate and 175 mg of 4-dimethylaminopyridine there is obtained 13-deoxy-22,23-dihydro-5-O-[bis-(2,2,2-trichloroethyl)-phosphono]avermectin B1a/B1b aglycone as a white foam.

EXAMPLE 28

13-Deoxy-22,23-dihydro-5-O-phosphono avermectin B1a/B1b aglycone

Following the procedure of Example 14 using 200 mg of 13-deoxy-22,23-dihydro-5-O-[bis-(2,2,2-trichloroethyl)phosphono]avermectin B1a/B1b aglycone, 6 ml of pyridine and 0.6 ml of 2,4-pentanedione and 0.3 g of the zinc-silver complex (as described in Example 3) there is obtained 13-deoxy-22,23-dihydro-5-O-phosphono avermectin B1a/B1b aglycone as a light foam.

EXAMPLE 29

13-Deoxy-22,23-dihydro-5-O-phosphono avermectin B1a/B1b aglycone monosodium salt Following the procedure of Example 15 using 100 mg (0.155 mmol) of 13-deoxy-22,23-dihydro-5-O-phosphono avermectin B1a/B1b aglycone and 6.2 ml of 0.025 M aqueous sodium hydroxide solution there is obtained 13-deoxy-22,23-dihydro-5-O-phosphono avermectin B1a/B1b aglycone monosodium salt as a fluffy lyophilate.

EXAMPLE 30

13-Deoxy-22,23-dihydro-4a-hydroxy-4a-O-[bis-2,2,2-trichloroethyl)phosphono]avermectin B1a/B1b aglycone Following the procedure of Example 1 using 100 mg of 13-deoxy-22,23-dihydro-4a-hydroxy avermectin B1a/B1b aglycone, 1.0 ml of tetrahydrofuran 110 mg (150 μl) of di-isopropylethylamine, 77 mg of bis-(2,2,2-trichloroethyl)phosphorochloridate, and 20 mg of 4-dimethylaminopyridine there is obtained 13-deoxy-22,23-dihydro-4a-hydroxy-4a-O-[bis-2,2,2-trichloroethyl)phosphono]avermectin B1a/B1b aglycone characterized by nuclear magnetic resonance and mass spectroscopy.

EXAMPLE 31

13-Deoxy-22,23-dihydro-4a-hydroxy-4a-O-phosphono avermectin B1a/B1b aglycone Following the procedure of Example 14 using 100 mg of 13-deoxy-22,23-dihydro-4a-hydroxy-4a-O-[bis-(2,2,2-trichloroethyl)phosphono]avermectin B1a/B1b aglycone, 3 ml of pyridine, 0.3 ml of 2,4-pentanedione, and 0.2 g of zinc-silver complex (prepared as in Example 3) there is obtained 13-deoxy-22,23-dihydro-4a-hydroxy-4a-O-phosphono avermectin B1a/B1b aglycone as a light foam.

What is claimed is:

1. A compound having the formula:

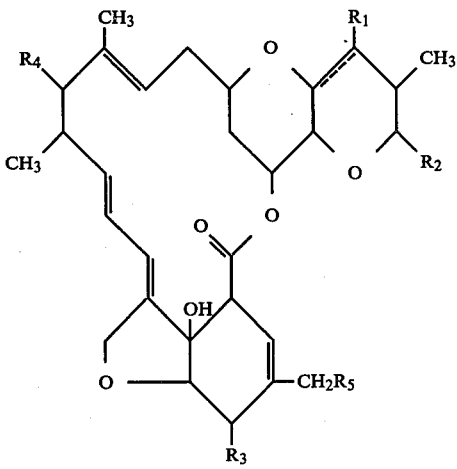

wherein the broken line indicates a single or a double bond;

wherein $R_1$ is H, loweralkanoyloxy, OH, =O or OR provided that $R_1$ is present only when the broken line indicates a single bond;

$R_2$ is methyl, ethyl, iso-propyl or sec-butyl;

$R_3$ is OH, OCH$_3$, loweralkanoyloxy, or OR;

$R_4$ is H, OH, OR, loweralkanoyloxy, α-L-oleandrosyloxy, 4'-(α-L-oleandrosyl)α-L-oleandrosyloxy, 4'-loweralkanoyl-αL-oleandrosyloxy, 4''-loweralkanoyl-4'-(α-L-oleandrosyl)-α-L-oleandrosyloxy,

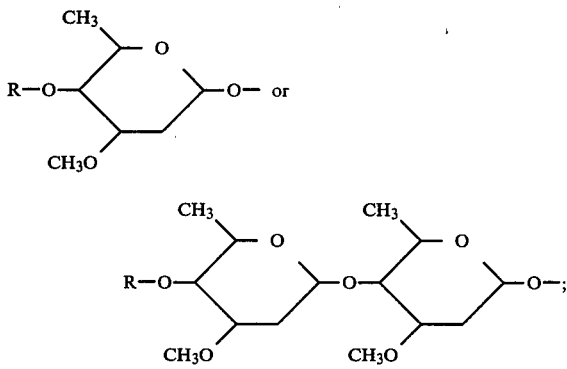

$R_5$ is H, or OR; and

R is P(O)(OH)(OMe), P(O)(OMe)$_2$, P(O)(OCH$_2$CCl$_3$)$_2$, P(O) (OH)$_2$, P(O)(OH)(OM), P(O)(OM)$_2$, P(O)(OH)—O$^-$(H$_3$N$^+$-alk), P(O)(O$^-$)$_2$(H$_3$N$^+$alk)$_2$, wherein M is an alkali metal, Me is methyl and alk is a loweralkyl; and physiologically acceptable salts thereof provided at least one of $R_1$, $R_3$, $R_4$ and $R_5$ contains a phosphate group of the R substituent.

2. The compound of claim 1 wherein R is: P(O)(OCH$_2$CCl$_3$)$_2$.

3. The compound of claim 2 which is 4''-O-acetyl-5-O-[bis-(2,2,2-trichloroethyl)phosphono] avermectin B1a or B1b.

4. The compound of claim 1 which is 4'',5-di-O-phosphono-23-keto-avermectin B2a or B2b.

5. The compound of claim 2 which is 22,23-dihydro-4'',5-di-O-[bis-(2,2,2-trichloroethyl)phosphono] avermectin B1a or B1b.

6. The compound of claim 2 which is 22,23-dihydro-4''-O-[bis-(2,2,2-trichloroethyl)phosphono] avermectin B1a or B1b.

7. The compound of claim 1 which is 22,23-dihydro-4''-O-phosphono avermectin B1a or B1b.

8. The compound of claim 1 which is 22,23-dihydro-4''-O-phosphono avermectin B1a or B1b monosodium salt.

9. The compound of claim 1 which is 4''-O-phosphono avermectin B1a or B1b.

10. The compound of claim 1 which is 4'',5-di-O-phosphono avermectin B1a or B1b.

11. The compound of claim 1 which is 13-deoxy-22,23-dihydro-5-O-phosphono avermectin B1a or B1b aglycone.

12. The compound of claim 1 which is 13-deoxy-22,23-dihydro-4a-hydroxy-4a-O-phosphono avermectin B1a or B1b aglycone.

13. The compound of claim 1 which is 22,23-dihydro-5-O-phosphono avermectin B1a or B1b.

14. The compound of claim 1 which is 5-O-phosphono avermectin B1a or B1b.

15. The compound of claim 1 which is 22,23-dihydro-4'-O-phosphono avermectin B1a or B1b monosaccharide.

16. The compound of claim 1 which is 4''-O-phosphono avermectin B2a or B2b.

17. The compound of claim 1 which is 22,23-dihydro-4'',5-di-O-phosphono avermectin B1a or B1b.

18. A method for the treatment of parasitic infections which comprises administering to an animal infected with parasites an effective amount of a compound of claim 1.

19. A composition useful for treating animals infected with parasites which comprises an inert carrier and a compound of claim 1.

* * * * *

UNITED STATES PATENT AND TRADEMARK OFFICE
CERTIFICATE OF CORRECTION

PATENT NO. : 4,469,682
DATED : September 4, 1984
INVENTOR(S) : H. H. Mrozik

It is certified that error appears in the above—identified patent and that said Letters Patent is hereby corrected as shown below:

Delete the first structure in Claim 1 on column 21 and replace it with the following:

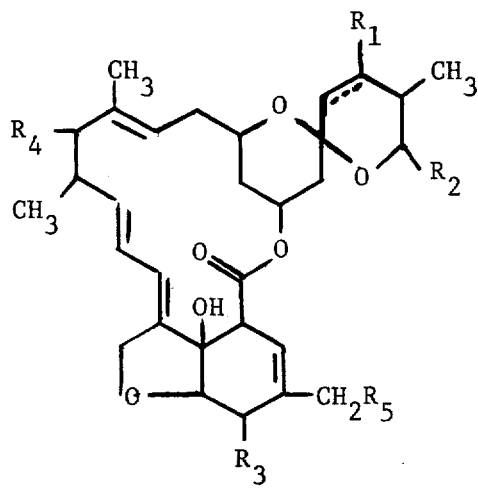

Signed and Sealed this

Second Day of April 1985

[SEAL]

Attest:

DONALD J. QUIGG

Attesting Officer    Acting Commissioner of Patents and Trademarks